United States Patent
Kang et al.

(10) Patent No.: US 11,967,440 B2
(45) Date of Patent: Apr. 23, 2024

(54) PASTE FOR REFERENCE ELECTRODE, REFERENCE ELECTRODE, AND BIOSENSOR INCLUDING THE SAME

(71) Applicant: I-SENS, INC., Seoul (KR)

(72) Inventors: Young Jea Kang, Seoul (KR); In Seok Jeong, Seoul (KR); Chul Hyun Park, Gyeonggi-do (KR); Suk Joon Kim, Seoul (KR); Yoon Beom Park, Seoul (KR)

(73) Assignee: I-SENS, INC., Seoul (KR)

( * ) Notice: Subject to any disclaimer, the term of this patent is extended or adjusted under 35 U.S.C. 154(b) by 0 days.

(21) Appl. No.: 17/735,275

(22) Filed: May 3, 2022

(65) Prior Publication Data

US 2022/0359100 A1  Nov. 10, 2022

(30) Foreign Application Priority Data

May 6, 2021 (KR) .......................... 10-2021-0058561

(51) Int. Cl.
*H01B 1/22* (2006.01)
*A61B 5/259* (2021.01)
*G01N 27/30* (2006.01)

(52) U.S. Cl.
CPC .............. *H01B 1/22* (2013.01); *A61B 5/259* (2021.01); *G01N 27/301* (2013.01)

(58) Field of Classification Search
CPC . H01B 1/22; C09D 5/24; A61B 5/259; G01N 27/301
See application file for complete search history.

(56) References Cited

U.S. PATENT DOCUMENTS

| | | | |
|---|---|---|---|
| 4,303,740 A | 12/1981 | Petro et al. | |
| 4,369,820 A | 1/1983 | Ahlers et al. | |
| 5,928,571 A * | 7/1999 | Chan | A61N 1/0436 252/514 |
| 2016/0033438 A1 | 2/2016 | Lan et al. | |
| 2016/0130471 A1* | 5/2016 | Burrows | H05K 1/0326 252/514 |
| 2019/0139670 A1* | 5/2019 | Shinohara | H01B 1/22 |

(Continued)

FOREIGN PATENT DOCUMENTS

| CN | 106291015 A | 1/2017 |
|---|---|---|
| CN | 113697843 A * | 11/2021 |
| JP | S55-050342 A | 4/1980 |

(Continued)

OTHER PUBLICATIONS

JP 1996094573 (pub date Apr. 1996) English language machine translation.*

(Continued)

*Primary Examiner* — Mark Kopec
(74) *Attorney, Agent, or Firm* — PLEECHAE IP, LLC

(57) ABSTRACT

A paste for a reference electrode according to an embodiment of the present disclosure includes silver chloride powder and a carbon-based conductive material. The carbon-based conductive material may include at least one compound selected from the group consisting of carbon nanotubes, graphite, graphene, and carbon black. The reference electrode formed of the paste for a reference electrode according to an exemplary embodiment may provide improved mechanical properties and electrochemical properties.

5 Claims, 1 Drawing Sheet

(56) References Cited

U.S. PATENT DOCUMENTS

2019/0307350 A1    10/2019  Sridhar et al.
2021/0159490 A1*    5/2021  Ossonon ................ H01G 9/042

FOREIGN PATENT DOCUMENTS

| JP | S56-142189 A | 11/1981 |
| JP | H08-094573 A | 4/1996 |
| JP | 3453904 B2 | 10/2003 |
| JP | 2004-279341 A | 10/2004 |
| JP | 2018-168445 A | 11/2018 |
| KR | 10-0170039 B1 | 2/1999 |
| KR | 10-1637325 B1 | 7/2016 |
| KR | 10-2016-0109806 A | 9/2016 |
| KR | 10-2018-0104070 A | 9/2018 |
| WO | WO 01/04614 A1 | 1/2001 |

OTHER PUBLICATIONS

Office action dated Apr. 4, 2023 from Japan Intellectual Property Office in a counterpart Japanese Patent Application No. 2022-075899 (all the cited references are listed in this IDS.) (English translation is also submitted herewith.).

European Search Report For EP22169744.4 dated Sep. 28, 2022 from European patent office in a counterpart European patent application.

Fernandes J.C. B. et al., "Alternative strategy for manufacturing of all-solid-state reference electrodes for potentiometry", Journal of Sensors and Sensor Systems, vol. 4, No. 1, Jan. 2015, pp. 53-61, XP055808303, DOI: 10.5194/jsss-4-53-2015.

Office action dated May 15, 2023 from Korean Patent Office in a counterpart Korean Patent Application No. 10-2021-0058561 (all the cited references are listed in this IDS.) (English translation is also submitted herewith.).

Kim, Tae Yong et al., "A solid-state thin-film Ag/AgCl reference electrode coated with graphene oxide and its use in a OH sensor", Sensors, Mar. 17, 2015, vol. 15 No. 3, pp. 6469-6482; doi:10.3390/s150306469.

Office action dated Aug. 29, 2023 from Australian Government Intellectual Property Office in a counterpart Australian Patent Application No. 2022202498.

Office action dated Jul. 25, 2023 from Japan Intellectual Property Office in a counterpart Japanese Patent Application No. 2022-075899 (English translation is also submitted herewith.).

Notice of Allowance issued on Jan. 25, 2024 Korean Patent Office in a counterpart Korean Patent Application No. 10-2021-0058561 (all the cited references are listed in this IDS.) (English translation is also submitted herewith.).

* cited by examiner

PASTE FOR REFERENCE ELECTRODE, REFERENCE ELECTRODE, AND BIOSENSOR INCLUDING THE SAME

CROSS-REFERENCE TO RELATED APPLICATION

This application claims the benefit under 35 USC § 119 of Korean Patent Application No. 10-2021-0058561, filed on May 6, 2021, in the Korean Intellectual Property Office, the entire disclosure of which is incorporated herein by reference for all purposes.

BACKGROUND

1. Field of the Invention

The present invention relates to a paste for a reference electrode, a reference electrode, and a biosensor including the same, and more particularly, to a reference electrode including silver chloride, and a biosensor including the reference electrode.

2. Description of the Related Art

Recently, patients with chronic diseases such as diabetes are increasing, and there is growing concern about the chronic diseases. As an extension thereof, demand for biosensors capable of monitoring a body composition, etc. to manage the chronic diseases is also steadily increasing. For example, by regularly performing a blood sugar check, it is possible for diabetic patients to control blood sugar levels more strictly and prevent complications from occurring.

A continuous blood sugar meter corresponding to an example of the biosensor may include a sensor module configured to measure a glucose concentration from a body fluid, and a transmitter configured to transmit a value measured by the sensor module to a terminal, wherein the value received from the transmitter is output by the terminal. In addition, the sensor module may further include a sensor probe, and the like to extract interstitial fluid, etc. from subcutaneous fat.

Meanwhile, the sensor module of the biosensor may include two or more electrodes to measure an electrical signal caused by a specific component of the body fluid. For example, the sensor module may include a working electrode and a reference electrode, and may further include a counter electrode. In particular, the sensor module may include the reference electrode to secure consistency in measurement.

As in Korean Patent Registration Publication No. 10-1637325, an invention for preventing deterioration of the sensor module is disclosed in the prior art. The sensor unit of Patent Document 1 further includes a filter unit. The filter unit is intended to prevent immune cells or other cells and biological particles or proteins contained in a living tissue or whole blood from being adsorbed to a working electrode (as a detection electrode) and a reference electrode (as a standard electrode).

However, Korean Patent Registration Publication No. 10-1637325 does not provide a special advantage in maintaining the consistency in signal measurement of biosignals by using the conventional electrodes.

SUMMARY

An object of the present invention is to provide a paste for a reference electrode having improved mechanical stability, a reference electrode and a biosensor including the same.

Another object of the present invention is to provide a paste for a reference electrode having improved electrical properties, a reference electrode and a biosensor including the same.

To achieve the above objects, the following technical solutions are adopted in the present invention.

1. A paste for a reference electrode, including a mixture of silver chloride powder and a carbon-based conductive material.
2. The paste for a reference electrode according to the above 1, wherein the paste does not comprise solid silver.
3. The paste for a reference electrode according to the above 1, wherein the carbon-based conductive material includes at least one compound selected from the group consisting of carbon nanotubes, graphite, graphene, and carbon black.
4. The paste for a reference electrode according to the above 3, wherein the carbon-based conductive material is included in an amount of 1 to 250 parts by weight based on 100 parts by weight of the silver chloride powder.
5. The paste for a reference electrode according to the above 1, wherein the silver chloride powder and the carbon-based conductive material are electrically connected with each other.
6. The paste for a reference electrode according to the above 1, wherein the mixture further comprises a resin.
7. A reference electrode including: a substrate; and an electrode layer formed of the paste for a reference electrode according to the above 1 on the substrate.
8. A biosensor including: a working electrode; and the reference electrode according to the above 7.
9. The biosensor according to the above 8, further including a counter electrode.

According to embodiments of the present invention, the paste for a reference electrode including the carbon-based conductive material is easily shaped, such that it is possible to implement the reference electrode without limitation on an external shape thereof by using the paste.

In addition, the reference electrode formed of the paste for a reference electrode according to the exemplary embodiment may provide improved mechanical properties.

Further, the reference electrode formed of the paste for a reference electrode according to the exemplary embodiment may provide improved electrical properties.

Furthermore, the reference electrode formed of the paste for a reference electrode according to the exemplary embodiment may include a carbon-based conductive material by replacing expensive solid silver with a low cost material such as a carbon-based conductive material, thereby providing an advantage in terms of production costs.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
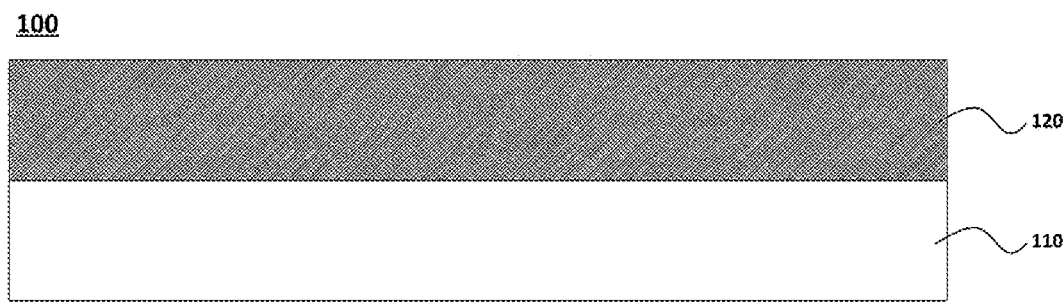
FIG. 1 is a schematic cross-sectional view illustrating a reference electrode according to an exemplary embodiment.

As used herein, the term "biosignal" may refer to a specific substance contained in a biosample, for example, a substance such as blood sugar, cholesterol, protein, hormone and the like. As an example of biosignal measurement, measurement of a glucose concentration contained in the interstitial fluid may be considered.

As used herein, the term "measurement" may refer to quantitatively analyzing a content of the specific substance.

Embodiments of the present invention disclose a paste for a reference electrode including a mixture of silver chloride powder and a carbon-based conductive material. Hereinafter, each configuration of the paste for a reference electrode will be described in more detail.

In embodiments of the present invention, the carbon-based conductive material may include at least one compound selected from the group consisting of carbon nanotubes (CNT), graphite (GP), graphene, and carbon black.

In some exemplary embodiments, by including the carbon-based conductive material, electrical conductivity and mechanical stability of the paste for a reference electrode, such as tensile strength, flexibility, elasticity, etc. may be improved.

The "carbon nanotube" is a carbon allotrope composed of carbon that exists in large amounts on earth, and means a material in which one carbon is bonded with other carbon atoms in a hexagonal honeycomb pattern to form a tube shape. The carbon nanotube has a particle diameter in a nano-size. The nano-size may mean a size between several nanometers and several tens of nanometers.

In some exemplary embodiments, the carbon nanotubes may have a single-walled, double-walled, or multi-walled shape, and may be formed in a rope shape in some cases. Since field emission characteristics can be maintained even when the carbon nanotubes having the wall shape are subjected to additional surface modification or adsorption, the paste for a reference electrode according to some exemplary embodiments may include multi-walled carbon nanotubes, or may include a mixture of single-walled carbon nanotubes and multi-walled carbon nanotubes.

As a method of synthesizing carbon nanotubes, an electric discharge method, a thermal decomposition method, a laser deposition method, a plasma chemical vapor deposition method, a thermochemical vapor deposition method, an electrolysis method, a flame synthesis method, and the like may be considered.

In some exemplary embodiments, by including carbon nanotubes as the carbon-based conductive material, electrical conductivity and mechanical stability such as flexibility of the paste for a reference electrode may be further improved.

The "graphene" is a material in which one carbon is bonded to other carbon atoms in a hexagonal honeycomb pattern to form a layer, and has high electrical conductivity and mechanical stability. The "graphite" is a carbon allotrope composed of carbon that exists in large amounts on earth, and means a material in which two or more types of graphene is laminated.

The number of sheets (single graphene layers) included in the graphite is preferably 2 to 100. When the number of sheets exceeds 100, excessive use of the carbon-based conductive material may be involved in order to implement uniform electrical properties, and workability of the paste for a reference electrode may be deteriorated. Therefore, the number of sheets (single graphene layers) included in the graphite is preferably 50 or less, more preferably 20 or less, and most preferably 10 or less.

The "carbon black" is a material obtained from incomplete combustion of a carbon-based compound such as tar, and includes Denka black, acetylene black, Ketjen black, Furnace black, Super-P black, thermal black and the like. Carbon black contains nano-sized fine particles.

In some exemplary embodiments, since the carbon black is used as the carbon-based conductive material, the carbon-based conductive material and the silver chloride powder may be more uniformly mixed with each other.

Embodiments of the present invention disclose a paste for a reference electrode including the carbon-based conductive material instead of solid silver. The carbon-based conductive material used instead of silver may come into contact with the silver chloride powder to be electrically connected thereto, such that a change in the silver chloride phase (e.g., generation of an electric current) caused by a measurement target may be electrically transmitted to a substrate or the like.

In addition, in exemplary embodiments, since the paste for a reference electrode do not have solid silver, a process for depositing or synthesizing silver chloride on the surface of silver may not be involved. In particular, a paste for a reference electrode having uniform interfacial properties may be prepared by a method of mixing the carbon-based conductive material with separately prepared silver chloride.

In addition, the paste for a reference electrode according to embodiments of the present invention may not include solid silver. Therefore, even if the reference electrode manufactured according to the embodiments is used together with a chlorine ion solution (e.g., KCl solution), etc., additional generation of silver chloride may be suppressed, and generation of $AgCl_2^-$ caused by an increase in the content of silver chloride may be delayed. Further, a change in the reference potential caused by additional generation of silver chloride, etc. may be suppressed, and a life-span of the reference electrode may be extended.

In addition, the paste for a reference electrode of exemplary embodiments includes powdery silver chloride. For example, the powdery silver chloride may refer to an aggregation of silver chloride particles. The silver chloride powder may include silver chloride particles. The silver chloride particles may have an aspect ratio of 0.5 or more, but it is preferable that the aspect ratio of the silver chloride particles is 0.9 or more, and more preferably a spherical or similar spherical shape in terms of capable of providing a uniform reference potential.

Further, according to some exemplary embodiments, the silver chloride particles may have an average particle diameter of 1 μm to 10 mm, preferably 1 μm to 1 mm, more preferably 1 μm to 100 μm, and most preferably 1 μm to 10 μm. As the average particle diameter of silver chloride is increased, a risk in which the silver chloride particles will not be uniformly dispersed in the carbon-based conductive material is increased, and as the average particle diameter of silver chloride is decreased, a risk in which the oxidation-reduction potential will not be constantly maintained is increased.

According to some exemplary embodiments, when the average particle diameter of the silver chloride particles exceeds 10 μm, a surface energy of the silver chloride particles is increased, such that the silver chloride particles may not be sufficiently dispersed by the carbon-based conductive material, and a shortage of mechanical stability such as an adhesion strength may be further increased. On the other hand, when the average particle diameter of the silver chloride particles is less than 1 μm, the surface of the silver chloride particles cannot be sufficiently exposed to an outside, such that electrochemical properties thereof as a reference electrode may be further deteriorated.

Therefore, since both electrochemical properties and mechanical stability of the reference electrode can be pursued, the powdery silver chloride preferably includes silver chloride particles satisfying the above-described numerical range.

In order to obtain silver chloride having a uniform average particle diameter, a conventional microemulsion method or matrix-based synthesis method known in the art may be used. In addition, a method of mixing silver nitrate ($AgNO_3$) and silver chloride to form aggregation nuclei, followed by growing the same may be used.

For example, when a molar ratio of hydrochloric acid to silver nitrate is 2 to 30, a silver chloride cube or sphere may be formed, and a hypothetical inscribed sphere or the sphere may have an average particle diameter of 1.5 μm to 0.05 mm.

In addition, in some exemplary embodiments of the paste for a reference electrode, the carbon-based conductive material may be included in an amount of 0.1 to 300 parts by weight ('wt. parts'), and preferably 1 to 250 wt. parts based on 100 wt. parts of the silver chloride powder.

According to some exemplary embodiments, when the silver chloride powder is included in an amount of less than 1 wt. part, a sufficient oxidation-reduction potential required for the reference electrode may not be secured. In addition, the oxidation-reduction potential may not be constantly maintained, and as a result of life-span evaluation, the reference electrode obtained therefrom may have a significantly short life-span below the reference. On the other hand, when the silver chloride powder is included in an amount exceeding 100 wt. parts, the evaluation result of mechanical stability of the reference electrode, for example, flexibility, may be below the reference due to the lack of the content of the carbon-based conductive material.

Therefore, since both electrochemical properties and mechanical stability of the reference electrode can be pursued, it is preferable that the paste for a reference electrode includes silver chloride powder in an amount of satisfying the above-described numerical range.

In addition, in exemplary embodiments, the paste for a reference electrode may further include a solvent to uniformly mix the silver chloride powder and the carbon-based conductive material included therein. Further, after the silver chloride powder and the carbon-based conductive material are uniformly mixed with each other, the solvent may be evaporated.

According to exemplary embodiments, the solvent is capable of dissolving a resin monomer, the carbon-based conductive material, and the silver chloride powder, and preferably has a polarity. As examples of the solvent, it may be considered to use at least one solvent of acetone, methyl ethyl ketone, methyl alcohol, ethyl alcohol, isopropyl alcohol, butyl alcohol, ethylene glycol, polyethylene glycol, tetrahydrofuran, dimethylformamide, dimethylacetamide, N-methyl-2-pyrrolidone, hexane, cyclohexanone, toluene, chloroform, distilled water, dichlorobenzene, dimethylbenzene, trimethylbenzene, pyridine, methylnaphthalene, nitromethane, acrylonitrile, octadecylamine, aniline, or dimethylsulfoxide.

In addition, in exemplary embodiments, the paste for a reference electrode may further include a resin. The resin functions as a binder, and by including the resin, the paste for a reference electrode may have an increased adhesiveness. Furthermore, by including a curable resin, the paste for a reference electrode may be cured in a predetermined shape.

Exemplary embodiments of the present invention disclose a paste for a reference electrode in which a mixture including silver chloride and the carbon-based conductive material further includes a resin.

As examples of the resin included in the mixture, it may be considered to use at least one of a polycarbonate resin, polyarylate resin, polysulfone resin, polystyrene resin, polyacrylate resin, styrene-acrylic copolymer, ethylene-vinyl acetate copolymer, polypropylene resin, olefin polymer, polyvinyl chloride resin, vinyl chloride-vinyl acetate copolymer, polyester resin, alkyd resin, polyamide resin, polyurethane resin, epoxy resin, diallyl phthalate resin, silicon resin, ketone resin, polyvinyl butyral resin, polyether resin, or phenol resin.

In addition, the curable resin may be a photocurable or thermosetting resin, and a pressure may be applied to the paste for a reference electrode during a curing process, or the pressure may be applied to the paste for a reference electrode before and after the curing process.

For example, the photocurable resin may include at least one of a monomer, an oligomer (or a resin, in particular, a low molecular weight resin), and a polymer. In addition, as an example of the monomer, a monofunctional monomer, or a polyfunctional monomer having at least two polymerizable unsaturated bonds may be considered.

As examples of the monofunctional monomer, (meth) acrylic monomers such as (meth)acrylic acid ester, etc.; vinyl monomers such as vinylpyrrolidone, (meth)acrylate having a bridged cyclic hydrocarbon group, such as isobornyl(meth)acrylate, adamantly(meth)acrylate, and the like may be considered.

In addition, as examples of the polyfunctional monomer, alkylene glycol di(meth)acrylate such as ethylene glycol di(meth)acrylate, propylene glycol di(meth)acrylate, etc.; (poly)oxyalkylene glycol di(meth)acrylate such as diethylene glycol di(meth)acrylate, dipropylene glycol di(meth) acrylate, etc.; di(meth)acrylate having a bridged cyclic hydrocarbon group, such as tricyclodecane dimethanol di(meth)acrylate, adamantane di(meth)acrylate, etc.; polyfunctional monomers having a polymerizable unsaturated bond, such as trimethylolpropane tri(meth)acrylate, trimethylolethane tri(meth)acrylate, pentaerythritol tri (meth)acrylate, and the like may be considered.

In addition, the curable resin may further include a curing agent according to types thereof. When using the thermosetting resin, a curing agent such as amines, polyvalent carboxylic acids, etc. may be commercially used. When using the photocurable resin, a photo-polymerization initiator may be included.

Further, as examples of the photo-polymerization initiator, acetophenones or propiophenones, benzils, benzoins, benzophenones, thioxanthones, acylphosphine oxides, and the like may be considered. In terms of securing both sufficient curing speed and mechanical properties, a content of the curing agent is preferably 0.1 to 20 wt. parts based on 100 wt. parts of a precursor of the curable resin.

In the present disclosure, embodiments of the present invention further disclose a reference electrode including: a substrate; and an electrode layer formed of the paste for a reference electrode according to exemplary embodiments on the substrate.

In addition, the substrate may have conductivity or include a layer having conductivity, or may not have conductivity. The substrate may have a shape of a foil, sheet or plate, and may be a single layer or multilayer.

For example, the substrate may include metal or a polymer resin. As examples of the metal, copper, zinc, nickel, cobalt, palladium, platinum, tin, stainless steel, or an alloy thereof may be considered. In addition, as examples of the polymer resin, polyethylene, polypropylene, polyimide (e.g., KAPTON®), polyethylene terephthalate (PET), polyacrylate, polycarbonate, silicone, epoxy resin, polyester (e.g., MYLAR®), polyethersulfone (PES), polyetherimide (e.g., ULTEM®), polyethylenenaphthalate (PEN), and the like may be considered.

In the present disclosure, embodiments of the present invention further disclose a biosensor including a working electrode and the reference electrode according to exemplary embodiments, and a biosensor including a working electrode, a counter electrode, and the reference electrode according to exemplary embodiments.

In some exemplary embodiments, the working electrode or the counter electrode may be manufactured using metal or a carbon-based material. For example, as a non-limiting example of the working electrode or the counter electrode, the use of metal, metal oxide, carbon ink, graphite, glassy carbon, graphene, and the like may be considered.

In some exemplary embodiments, the biosensor may include a two-electrode system. In addition, in some exemplary embodiments, in order to further improve reliability and precision in measurement, the biosensor may employ a three-electrode system by further including a counter electrode.

According to exemplary embodiments, the biosensor may be used to measure the concentrations, etc., of various biomaterials. The measurement using the biosensor may be performed based on a change in current according to the presence of the measurement target and the concentration thereof. In addition, the reference electrode according to an exemplary embodiment may provide a background value as a reference for measurement.

Further, as examples of the biomaterial to be the measurement target, enzyme, aptamer, carbohydrate, protein, oxide, lipid, hormone, DNA, PNA, RNA, or a mixture thereof may be considered. Furthermore, the biomaterial may be included in blood, urine, tears, sweat, saliva, intercellular fluid, lymph fluid, cerebrospinal fluid or the like.

In addition, the biosensor may be used to measure biological characteristics of a subject. An exemplary biosensor may be used to extract health information combining skin temperature, heart rate, respiration rate, or blood pressure.

Hereinafter, experimental examples including specific examples and comparative examples will be described to more concretely understand the present invention. However, those skilled in the art will appreciate that such examples are provided for illustrative purposes and do not limit subject matters to be protected as disclosed in appended claims. Therefore, it will be apparent to those skilled in the art various alterations and modifications of the embodiments are possible within the scope and spirit of the present invention and duly included within the range as defined by the appended claims.

Specifically, electrochemical properties and mechanical properties of the reference electrode according to exemplary embodiments will be described with reference to drawings and examples. However, it should be noted that such a description is provided to facilitate understanding of those skilled in the art, and is not intended to limit the scope of the present invention.

FIG. 1 is a schematic cross-sectional view illustrating a reference electrode according to an exemplary embodiment. A reference electrode 100 according to an exemplary embodiment includes a substrate 110 and an electrode layer 120 formed of the paste for a reference electrode according to the exemplary embodiment on the substrate. A method of manufacturing the reference electrode 100 according to an exemplary embodiment is the same as described in the following examples and comparative examples.

EXAMPLES AND COMPARATIVE EXAMPLES

Example 1

About 400 wt. parts of isobornyl acrylate monomer, 100 wt. parts of silver chloride having an average particle diameter of 3 μm, 200 wt. parts of graphite (CAS No. 7782-42-5, manufactured by Sigma Aldrich, GP), and 20 wt. parts of 2,4,6-trimethylbenzoyl-diphenyl-phosphine oxide were added in an excess organic solvent, and mixed well at 80° C. for 1 hour, then the solvent was evaporated to obtain a paste.

The obtained paste was applied to a PET substrate and irradiated with light (ultraviolet rays) to induce a photocuring reaction. As a result, a reference electrode in which silver chloride and graphite were uniformly mixed could be obtained.

Example 2

A paste was prepared by performing the same procedures as described in Example 1, except that silver chloride having an average particle diameter of 8 μm was used. In addition, about 600 wt. parts of isobornyl acrylate monomer and 200 wt. parts of graphite were used.

Example 3

A paste was prepared by performing the same procedures as described in Example 1, except that silver chloride having an average particle diameter of 15 μm was used. In addition, about 800 wt. parts of isobornyl acrylate monomer and 200 wt. parts of graphite were used.

Example 4

A paste was prepared by performing the same procedures as described in Example 1, except that silver chloride having an average particle diameter of 1 μm was used. In addition, about 200 wt. parts of isobornyl acrylate monomer and 200 wt. parts of graphite were used.

Example 5

A paste was prepared by performing the same procedures as described in Example 1, except that about 300 wt. parts of graphite was used.

Example 6

A paste was prepared by performing the same procedures as described in Example 1, except that about 150 wt. parts of graphite was used.

Example 7

A paste was prepared by performing the same procedures as described in Example 1, except that about 75 wt. parts of graphite was used.

Example 8

A paste was prepared by performing the same procedures as described in Example 1, except that about 10 wt. parts of graphite was used.

Example 9

A paste was prepared by performing the same procedures as described in Example 1, except that about 1 wt. part of graphite was used.

Example 10

A paste was prepared by performing the same procedures as described in Example 1, except that 150 wt. parts of graphene (CAS No. 1034343-98-0, manufactured by Sigma Aldrich) was mixed instead of 200 wt. parts of graphite.

Example 11

A paste was prepared by performing the same procedures as described in Example 1, except that 150 wt. parts of multi-walled carbon nanotubes (mw-CNT, CAS No. 308068-56-6, manufactured by Sigma Aldrich) was mixed instead of 200 wt. parts of graphite.

Example 12

A paste was prepared by performing the same procedures as described in Example 1, except that 200 wt. parts of Denka black (manufactured by Denka Korea Co., Ltd.) was mixed instead of 150 wt. parts of graphite.

Compositions and contents of the compounds included in the pastes of Examples 1 to 12 are summarized in Table 1 below. The numerical values indicated for each compound means wt. parts. The particle diameter means an average particle diameter of the silver chloride powder, and the unit is $\mu m$.

TABLE 1

| Con-figuration | Example | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Resin | 400 | 600 | 800 | 200 | 400 | 400 | 400 | 400 | 400 | 400 | 400 | 400 |
| Silver chloride powder | 100 | 100 | 100 | 100 | 100 | 100 | 100 | 100 | 100 | 100 | 100 | 100 |
| GP | 200 | 200 | 200 | 200 | 300 | 150 | 75 | 10 | 1 | — | — | — |
| Graphene | — | — | — | — | — | — | — | — | — | 150 | — | — |
| mw-CNT | — | — | — | — | — | — | — | — | — | — | 150 | — |
| Denka black | — | — | — | — | — | — | — | — | — | — | — | 150 |
| Particle diameter | 3 | 8 | 15 | 1 | 3 | 3 | 3 | 3 | 3 | 3 | 3 | 3 |

Comparative Example 1

A paste was prepared by performing the same procedures as described in Example 1, except that about 400 wt. parts of an isobornyl acrylate monomer and 100 wt. parts of silver chloride powder having an average particle diameter of 3 $\mu m$ were mixed.

Comparative Example 2

A paste was prepared by performing the same procedures as described in Example 1, except that about 400 wt. parts of isobornyl acrylate monomer, 200 wt. parts of graphite, 50 wt. parts of silver chloride powder having an average particle diameter of about 3 $\mu m$, and 50 wt. parts of silver powder having an average particle diameter of about 3 $\mu m$ were mixed.

Comparative Example 3

A paste was prepared by performing the same procedures as described in Example 1, except that about 400 wt. parts of an isobornyl acrylate monomer, 200 wt. parts of graphite, and 100 wt. parts of silver powder having an average particle diameter of 3 $\mu m$ were mixed.

Experimental Example

1. Life-Span Evaluation of Reference Electrode

The life-span of each of the reference electrodes manufactured using the pastes prepared according to the examples and comparative examples was evaluated using a potentiostat (CHI660). Each of the prepared reference electrodes was immersed in a phosphate buffered saline (PBS) solution to which 3M of potassium chloride (KCl) was added. In order to measure a potential value of the reference electrode, a silver/silver chloride electrode was used as a counter electrode. An initial value of the measured potential was 0.02 to 0.06 V.

Standards for evaluating the life-span of the reference electrode are as follows. The performance of each reference electrode was evaluated based on the period during which the initial value of the measured potential was maintained at a specific level or higher. The measurement of the electric potential was performed every one minute.

◉ (Excellent): The potential value exceeds 95% of the initial value for 45 days

○ (Favorable): The potential value exceeds 95% of the initial value for 30 days x (Below the reference): The potential value is below 95% of the initial value within 30 days.

Figure 2:
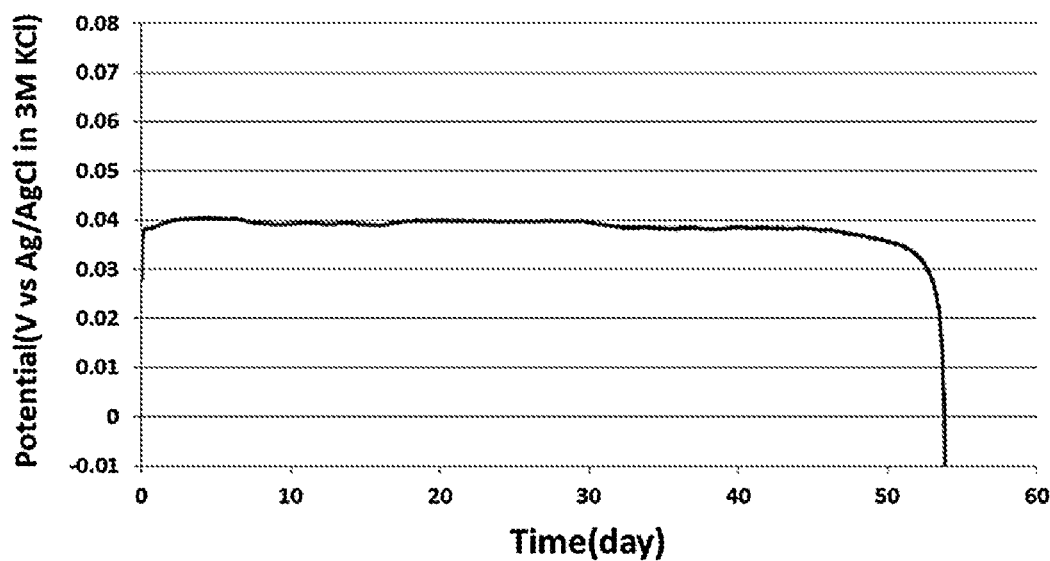
FIG. 2 is a graph illustrating a change in a potential value over time of the reference electrode according to an exemplary embodiment.

In addition, FIG. 2 is a graph illustrating a change in the potential value over time of the reference electrode obtained by using the paste for a reference electrode according to Example 1. The initial potential value was 0.04 V, and the current value was 10 nA.

Referring to FIG. 2, since a potential of about 0.04 V was maintained for 30 days or more and a potential value of 0.038 V or higher was maintained even after 45 days had elapsed in the reference electrode of Example 1, it was found that the life-span evaluation result of the electrode was excellent. In addition, results of the life-span evaluation of the electrodes of the examples and comparative examples are shown in Table 2 below.

TABLE 2

| Life-span evaluation result | | | | | | | | | | | | |
|---|---|---|---|---|---|---|---|---|---|---|---|---|
| | Example | | | | | | | | | | | |
| | 1 | 2 | 3 | 4 | 5 | 6 | 7 | 8 | 9 | 10 | 11 | 12 |
| Evaluation result | ◉ | ◉ | ○ | ◉ | ◉ | ◉ | ◉ | ◉ | ○ | ◉ | ◉ | ◉ |

| | Comparative Example | | |
|---|---|---|---|
| | 1 | 2 | 3 |
| Evaluation result | x | x | x |

Referring to Table 2, it can be seen that the reference electrodes of Examples 3 and 9 had favorable life-spans, and all of the reference electrodes of the examples except the above examples had excellent life-spans. Thereby, it is determined that the addition of the carbon-based conductive material up to a certain content contributes to an increase in the life-span.

On the other hand, all the reference electrodes of Comparative Examples 1 to 3 had life-spans below the reference, and in the reference electrodes of Comparative Examples 2 and 3, a change in the potential of 1% or higher was confirmed.

2. Adhesion Evaluation of Reference Electrode

The adhesion of the reference electrode was evaluated according to ISO 2409. In detail, 100 specimens were prepared by cross-cutting the cured products of the pastes obtained in the examples and comparative examples with a cutting machine having blades with an interval of 1 mm.

A test tape having an adhesive force of about 7.6 N/cm was attached to and detached from the prepared specimen, and the number of intact specimens was recorded. Adhesion evaluation results are shown in Table 3 below.

TABLE 3

| Adhesion evaluation result | | | | | | |
|---|---|---|---|---|---|---|
| Example | 1 | 2 | 3 | 4 | 5 | 6 |
| Evaluation result | 98 | 100 | 100 | 93 | 95 | 100 |
| Example | 7 | 8 | 9 | 10 | 11 | 12 |
| Evaluation result | 100 | 100 | 100 | 100 | 100 | 100 |
| Comparative Example | | 1 | | 2 | | 3 |
| Evaluation result | | 100 | | 100 | | 100 |

Referring to Table 3, it was found that the specimens of the cured products obtained from the examples except for Examples 1, 4 and 5, and the comparative examples remained intact even after the evaluation of the adhesion force. According to the evaluation results, it was confirmed that the number of intact specimens was increased as the content ratio of the resin included in the paste for a reference electrode was increased.

3. Flexibility Evaluation of Reference Electrode

In order to evaluate the flexibility of the reference electrode, 5 specimens having a size of 15 mm×25 mm were cut out from each of the cured products of the pastes obtained in the examples and comparative examples. According to JIS P 8115, each specimen was bent 5 times in a vertical direction, and a change in resistance before and after bending of the specimen was measured.

In bending of the specimen, a radius of curvature was 0.8 mm, a transmission speed was 175 rpm, a feed angle was 135 degrees, and a load was 0.5 kgf as detailed conditions. The standards for evaluation are as follows, and flexibility evaluation results are shown in Table 4 below.

◎ (Excellent): Resistance change before and after bending times is 5% or less

○ (Favorable): Resistance change before and after bending times is 10% or less x (Below the reference): resistance change before and after bending 5 times exceeds 10%

TABLE 4

| Flexibility evaluation result | | | | | | |
|---|---|---|---|---|---|---|
| Example | 1 | 2 | 3 | 4 | 5 | 6 |
| Evaluation result | ○ | ○ | x | ◎ | ◎ | ○ |
| Example | 7 | 8 | 9 | 10 | 11 | 12 |
| Evaluation result | ○ | ○ | x | ○ | ◎ | ○ |
| Comparative Example | | 1 | | 2 | | 3 |
| Evaluation result | | x | | ○ | | ○ |

Referring to Table 4, all the cured products of the examples except for Examples 3 and 9 were evaluated to have favorable flexibility or higher, and Examples 4, 5 and 11 were evaluated to have excellent flexibility. In addition, all the cured products of the comparative example except for Comparative Example 1 were also evaluated to have favorable flexibility.

Referring to the evaluation results, it was found that the higher the content ratio of the carbon-based conductive material included in the paste for a reference electrode, the better the flexibility. In addition, it was found that the flexibility may vary depending on the types of the carbon-based conductive material, and the use of carbon nanotubes may contribute to the improvement of the flexibility.

What is claimed is:

1. A biosensor comprising:
   a working electrode configured for measuring of a biosignal; and
   a reference electrode configured for providing a background value as a reference for the measuring, the reference electrode comprising a substrate and an electrode layer formed of a paste, the paste comprising a mixture of silver chloride powder and a carbon-based conductive material, the reference electrode being free from solid silver.

2. The biosensor according to claim 1, wherein the carbon-based conductive material includes at least one compound selected from the group consisting of carbon nanotubes, graphite, graphene, and carbon black.

3. The biosensor according to claim 2, wherein the carbon-based conductive material is included in an amount of 1 to 250 parts by weight based on 100 parts by weight of the silver chloride powder.

4. The biosensor according to claim 1, wherein the silver chloride powder and the carbon-based conductive material are electrically connected with each other.

5. The biosensor according to claim 1, further comprising a counter electrode.

* * * * *